United States Patent
Kane et al.

(10) Patent No.: US 9,063,541 B2
(45) Date of Patent: Jun. 23, 2015

(54) METHOD AND MEANS FOR TRACKING CORROSION-RELATED PLANT OPERATION COSTS

(75) Inventors: Russell D. Kane, Houston, TX (US); Yohki Kajiyama, Yokohama (JP)

(73) Assignee: Honeywell International Inc., Morristown, NJ (US)

( * ) Notice: Subject to any disclaimer, the term of this patent is extended or adjusted under 35 U.S.C. 154(b) by 1496 days.

(21) Appl. No.: 12/214,581

(22) Filed: Jun. 20, 2008

(65) Prior Publication Data

US 2009/0319084 A1    Dec. 24, 2009

(51) Int. Cl.
*G05B 21/00* (2006.01)
*G05B 23/02* (2006.01)
*G01N 17/02* (2006.01)
*G01N 17/04* (2006.01)

(52) U.S. Cl.
CPC ........ *G05B 23/0289* (2013.01); *G05B 23/0283* (2013.01); *G01N 17/02* (2013.01); *G01N 17/04* (2013.01)

(58) Field of Classification Search
CPC ... G01N 17/02; G01N 17/04; G05B 23/0283; G05B 23/0289
USPC .......................................................... 700/266
See application file for complete search history.

(56) References Cited

U.S. PATENT DOCUMENTS

| | | | |
|---|---|---|---|
| 6,047,241 A | 4/2000 | Sparago | |
| 6,487,518 B1 | 11/2002 | Miyazaki et al. | |
| 6,683,463 B2 * | 1/2004 | Yang et al. | 324/700 |
| 2005/0148081 A1 * | 7/2005 | Braunling et al. | 436/6 |
| 2008/0126033 A1 | 5/2008 | Meyer et al. | |

FOREIGN PATENT DOCUMENTS

| | | |
|---|---|---|
| EP | 0661538 A2 | 7/1995 |
| EP | 0727656 A1 | 8/1996 |
| JP | 2003-0303243 A | 10/2003 |

* cited by examiner

*Primary Examiner* — Jonathan Hurst

(57) ABSTRACT

A method of controlling corrosion-related plant operation costs is provided, the method including: accumulating real-time corrosion measurements relating to a plant operation; calculating a relative degree of corrosion value that includes consideration of the real-time corrosion measurements; comparing the relative degree of corrosion value to an expected corrosion progression value associated with a predetermined target maintenance cycle; and adjusting a plant operation based on a comparison of the relative degree of corrosion value to the expected corrosion progression value associated with a predetermined target maintenance cycle. An apparatus for controlling corrosion-related plant operation costs is also provided.

23 Claims, 2 Drawing Sheets

US 9,063,541 B2

METHOD AND MEANS FOR TRACKING CORROSION-RELATED PLANT OPERATION COSTS

FIELD OF THE INVENTION

The present invention relates generally to methods and means for tracking costs associated with the operation of an industrial plant, and in more particular though non-limiting embodiments, to methods and means for tracking and minimizing corrosion-related plant operation costs in various industrial environments.

BACKGROUND OF THE INVENTION

Traditionally, corrosion has not been treated as a process variable phenomenon. Thus, no significant effort has previously been made to perform plant operation analysis based on real-time corrosion measurements, or to identify the potential impact corrosion might have on plant operation, particularly from the standpoint of associated economic impact.

Even with the advent of computers and advanced process control techniques, plant operation analysis has largely been limited to measurement of conventional process variables, such as temperature, pressure, and flow rates; values obtained from on-line analyzers, for example, chemical composition data; and values derived from chemical engineering estimation formulas, for example, flood percentages, etc.

Such variables are typically considered as input/output variables in dynamic predictive control models designed to determine optimal plant operating conditions, which take into account the likely future impact of the variables with respect to the subject process.

To date, however, there has been no known attempt to provide a dynamic predictive control model that incorporates highly precise real-time corrosion measurements in such a manner that the corrosion-related factors are adequately considered in relation to the economic impact of corrosion on plant operation and maintenance costs.

SUMMARY OF THE INVENTION

A method of controlling corrosion-related plant operation costs is provided, said method comprising: accumulating real-time corrosion measurements relating to a plant operation; calculating a relative degree of corrosion value that includes consideration of said real-time corrosion measurements; comparing said relative degree of corrosion value to an expected corrosion progression value associated with a predetermined target maintenance cycle; and adjusting a plant operation based on the comparison of the relative degree of corrosion value to the expected corrosion progression value associated with a predetermined target maintenance cycle.

A means for controlling corrosion-related plant operation costs is also provided, said means comprising: means for accumulating real-time corrosion measurements relating to a plant operation; means for calculating a relative degree of corrosion value that includes consideration of said real-time corrosion measurements; means for comparing said relative degree of corrosion value to an expected corrosion progression value associated with a predetermined target maintenance cycle; and means for adjusting a plant operation based on the comparison of the relative degree of corrosion value to the expected corrosion progression value associated with a predetermined target maintenance cycle.

DETAILED DESCRIPTION OF THE INVENTION

Figure 1:
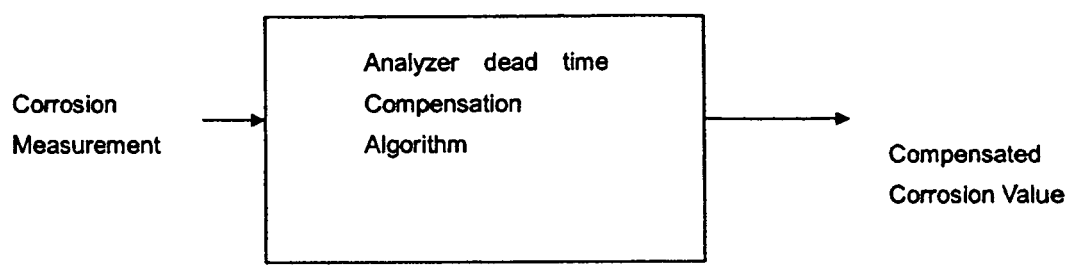
FIG. 1 depicts a dead-time analyzer system designed to derive compensated corrosion values from physical corrosion measurements using a compensation algorithm.

With reference now to FIG. 1, an on-line dead-time analyzer or the like can be used to record data indicative of instantaneous corrosion measurements obtained from high-precision corrosion sensors. By equipping the analyzer with a compensation algorithm and applying the compensation algorithm to the recorded corrosion data, compensated corrosion values can be acquired.

Figure 2:
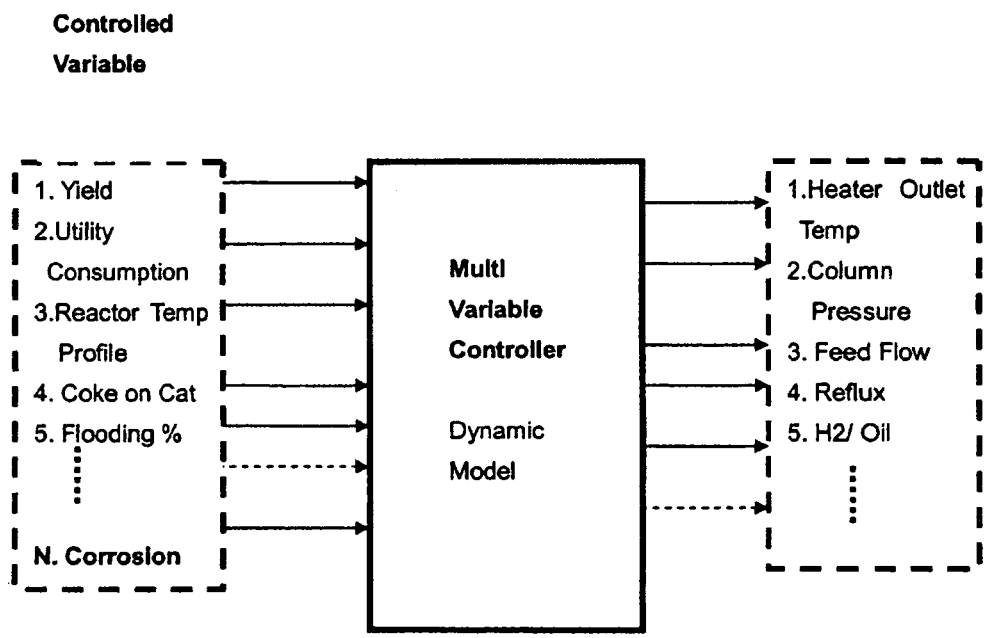
FIG. 2 depicts a multi-variable controller system designed to derive relative degree of corrosion values using a dynamic predictive control model and compensated corrosion values obtained from an analyzer.

Turning now to FIG. 2, the analyzer treats the compensated corrosion values like previously known control variables, for example, measurements derived from other physical components of the plant, such as a process input valve or a flow diverter, for purposes of improved predictive control modeling. Since improved predictive control modeling admits to more accurate and informative overall process measurements, a safer and more profitable operational environment are realized.

In the depicted embodiment, compensated corrosion values are treated as a control variable together with other important process indicators such as yield, utility consumption, the reactor temperature profile, flooding percentage, etc., and analyzed using a predictive control model in order to obtain additional composite values such as a heater outlet temperature, column pressure, feed flow rate, reflux, H2/Oil ratio, etc., in such a manner that corrosion rates become an integral part of the predictive model calculus. While the process variables and real-time measured corrosion rates share a certain inherent correlation, there are still degrees of difference in correlation between and amongst the respective process variables.

In a further embodiment, the integrated corrosion rates are used to identify the associated economic impact corrosion has on plant operation as a correlative index. By continuously monitoring the resulting index (e.g., corrosion rates, pitting factors, etc.) and making such information available to plant engineers and operators, the plant is run more safely, and more efficient unit operations is realized. This process is sometimes referred to as corrosion benchmarking, as a still further embodiment of the invention comprises a ranking of superior and inferior technical considerations based on a percentile or other numerically-based system.

While corrosion is not usually responsible for immediate plant shut down conditions, it will still degrade unit materials to varying degrees over time (depending in part on the variability of associated process conditions) and eventually result in the need for an unexpected plant shutdown. In order to avoid such an occurrence, corrosion should therefore be monitored and analyzed on a real-time basis at all times in order to prevent operational conditions that may cause unexpectedly pronounced corrosion conditions, and process variables should be continuously processed and analyzed on a real-time basis so that a plant equipped with such a system can maintain or even exceed a predetermined maintenance shut down schedule.

Figure 3:
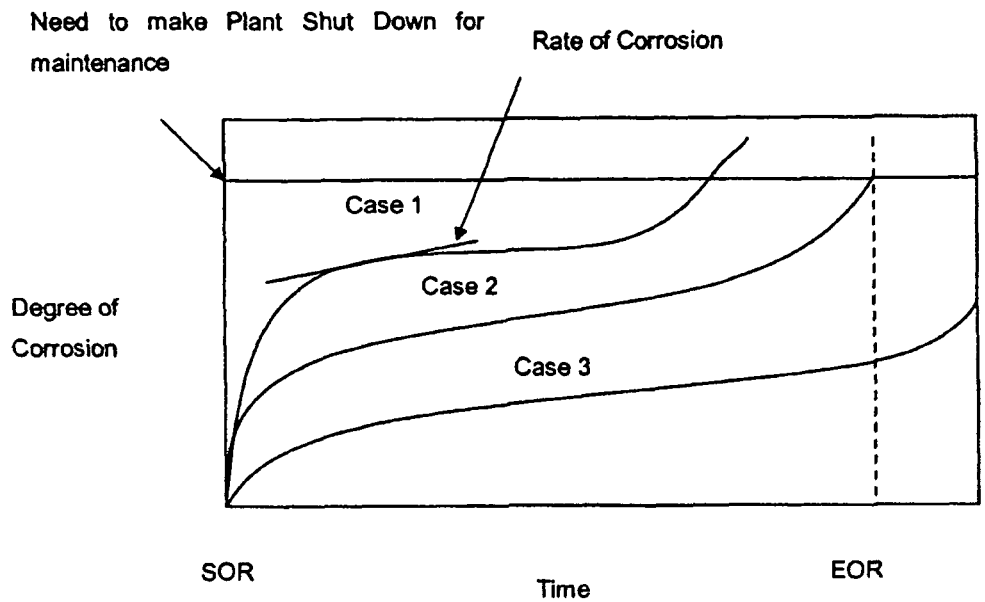
FIG. 3 is an X-Y axis graph showing the general relationship between corrosion and a plant maintenance cycle as a function of time.

According to one embodiment, a plot of the general relationship between corrosion and a plant maintenance or operational cycle as a function of time is provided in FIG. 3. Those of ordinary skill in the art will appreciate that the example embodiment of FIG. 3 conveys only a simple model of the relationship, and that the actual degree of corrosion (or instantaneous corrosion rate) may in fact vary much more as a function of time, depending on the specific process conditions and the extent to which those processes are controlled.

The dotted line in FIG. 3 indicates a normal scheduled maintenance event. In example Case 1, corrosion progresses faster than previously forecasted, thereby requiring an earlier plant shut down ("end of run") than originally planned. Case 2 provides the optimal model, in which cumulative corrosion and subsequent plant shut-down proceed with relatively unexpected variance. Finally, in Case 3, a situation where corrosion develops slower than expected is depicted, so that absent other deleterious factors, operations can be continued longer than the originally planned maintenance cycle would otherwise allow.

Mathematically, the total Corrosion C is considered to be a function $f$ of the various corrosion related variables:

$$C = f(\text{temperature, pressure, flow rate, feed rate} \ldots) \quad \{\text{Equation 1}\}.$$

It follows from Equation 1 that the rate of corrosion is defined by the change in corrosion C as a function of time:

$$\text{Rate of Corrosion} = d(C)/dt \quad \{\text{Equation 2}\}.$$

By including various corrosion rates as a function of time in a multi-controller predictive control schema, it becomes possible to regulate the corrosion rate so that it remains within a predetermined range of acceptable limits, and plant safety and extended plant operations are possible.

Separate from the underlying technical issues is the associated economics of plant operation. In this context, those economics are primarily determined by two factors: (1) operational profit, or profit derived from production activities, and (2) cost incurred by maintenance activities, and system component repair or replacement.

One formulation for determining plant profit is as follows:

$$\text{Operational Profit} = \sum \left[ \frac{(\text{Production Rate}) *}{(\text{Product Value})} \right] - \sum \left[ \frac{(\text{Utility Consumption}) *}{(\text{Utility Cost})} \right] - \sum \left[ \frac{(\text{Raw Material usage}) *}{(\text{Raw Material Cost})} \right]. \quad \{\text{Equation 3}\}$$

While reasonable practitioners might weigh these variables differently, it is probable that production rate and utility consumption—being functions of the process variables—are likely to have the most significant impact economically.

However, the expense associated with maintaining and managing a plant is also likely to be significantly impacted by costs associated with labor and maintenance, which includes labor and maintenance costs made necessary by corrosion-related conditions.

So, when considering the overall impact of corrosion on a plant's profitability, it can be reasonably concluded that corrosion rates have an impact on associated maintenance cycles, and thus should be considered in relation to the aforementioned economic factors.

With respect to corrosion's effect on productivity, it is frequently the case that operating under severe corrosion conditions will, at least over the short term, improve productivity, since continuing plant operations despite corrosion rates above predetermined levels of acceptability will lead to a temporary increase in production output. However, such conditions can also escalate marginal corrosion conditions to safety alert conditions as the rate of accumulated corrosion begins to accelerate, and should therefore be closely monitored.

Following from Equation 3 above, the impact on plant profit due to the cumulative effects of corrosion can be expressed as follows:

$$\Delta(\text{Plant Production})/\Delta(C) = \left[ \left( \frac{\Delta(\text{Production Rate})}{\Delta(C)} \right) * (\text{Product Value}) \right] - \left[ \left( \frac{\Delta(\text{Utility Consumption})}{\Delta(C)} \right) * (\text{Utility Cost}) \right] - \left[ \left( \frac{\Delta(\text{Raw Material Usage})}{\Delta(C)} \right) * (\text{Raw Material Cost}) \right] - \left[ (\text{Raw Material Usage}) * \left( \frac{\Delta(\text{Raw Material Cost})}{\Delta(C)} \right) \right]. \quad \{\text{Equation 4}\}$$

Figure 4:
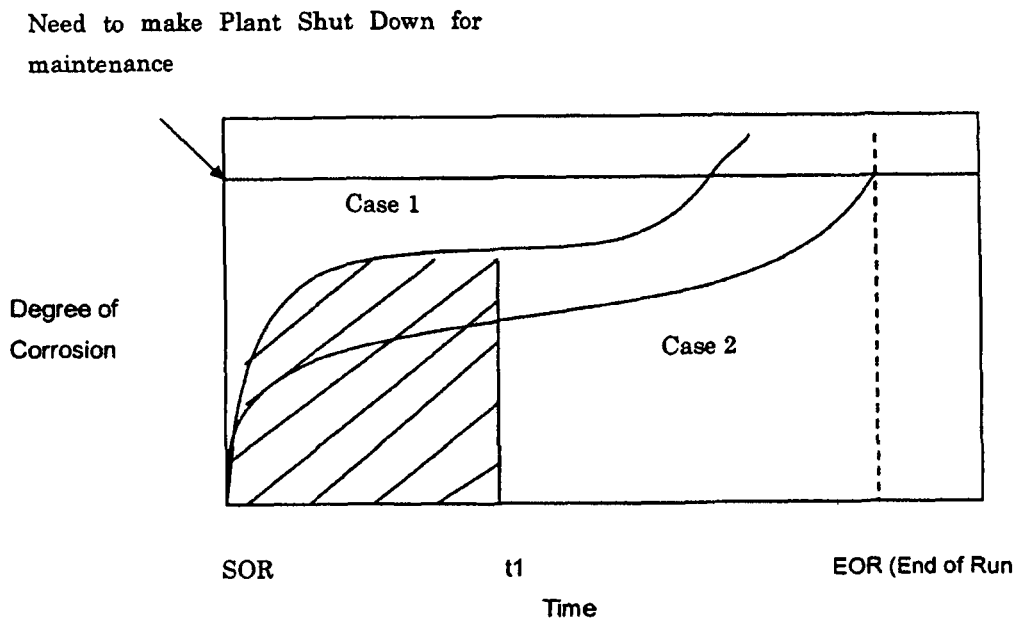
FIG. 4 is an X-Y axis graph showing the relationship between a derived relative degree of corrosion and a plant maintenance cycle as a function of time.

With regard to plant maintenance costs, if it is assumed that the corrosion rate and maintenance cycle share the relationship depicted in FIG. 3, the accumulated (or total) degree of corrosion at an arbitrary time t1 for Case 1 can be defined as follows:

$$C_{total} = \int_{t=0}^{t=1} d(C)/dt)_{Case\ 1} dt, \quad \{\text{Equation 5}\},$$

the resultant from which is defined by the shaded area in FIG. 4.

If it is assumed that the desired maintenance cycle's shut-down target is defined as Case 2, a relative degree of corrosion at time t=1 in Case 1 can be expressed as a percentage in accord with the following:

$$C(\%) = (\int_{t=0}^{t=1} d(C)/dt_{Case\ 1} dt / (\int_{t=0}^{t=1} EOR(d(C)/dt)_{Case\ 2} dt)) * 100, \quad \{\text{Equation 6}\}.$$

From the above analysis, one of ordinary skill in the art will conclude that when precision instruments are used to accumulate real-time corrosion measurements from the plant's Start of Run (SOR), calculated into the derived relative degree of corrosion, and then provided to plant operator, the operator will become aware of unexpected corrosion progression during the target maintenance cycle that will better enable safe and efficient operations, while extending plant runs and avoiding unexpected failures due to corrosion, thereby contributing to an improved overall operational efficiency.

For example, if a 1,000 day-period is assumed as a standard maintenance cycle, and if the relative degree of corrosion determined by Equation 6 were 50% on day 300 during ongoing operations, the EOR (End of Run) should be expected to come in 300 more days, thereby forcing maintenance to take place 400 days earlier than initially planned.

Since the plant operator is apprised of this fact at the earliest possible time, the option of continuing plant operations during this mode can be weighed against the option of continuing operations under a less corrosive situation, and the potentially hazardous conditions caused by corrosion-related factors can be closely monitored and mediated so that the target maintenance cycle is achieved.

Alternatively, should a negative deviation of corrosion be detected, and systems and components responsible for the situation are identified and better controlled early in the process while still meeting process productivity goals, there may be realized an unexpectedly beneficial situation wherein the maintenance cycle is extended while the plant continues to produce for a period beyond the originally planned maintenance cycle. Thus, it is found that by determining and supplying plant operators with real-time relative degree of corrosion values, operators will be better able to make operational decisions that lead to significant improvement in plant operations and profitability.

While the examples given above relate primarily to general corrosion management, a similar approach can be adopted to identify and control localized corrosion (i.e., pitting) by establishing a localized corrosion correlative value comprised of additional control variables (e.g., the corrosion rate and an associated pitting factor), and integrating the correlative value into the relative degree of corrosion value. Pitting is a particularly dangerous type of corrosion that has historically not been monitored in the normal course of process control, since the automated capability to perform such monitoring was only recently developed (for example, using the SmartCET monitoring system offered by Honeywell International, Inc.), and thus precise monitoring of pitting within the context of the presently claimed methodology is deemed highly advantageous from both a financial and safety perspective.

This embodiment is potentially significant, since the damage to plant operations is often highly localized, and can suddenly increase the overall corrosion progression rate by multiple orders of magnitude. Those of skill in the art will readily appreciate that such situations can very quickly have a large impact on operations and profitability due to the sudden and unexpected damage frequently associated with rapidly accumulated localized corrosion.

The integration of real-time assessments of corrosion factors and an advanced process control system capable of recognizing and reacting to corrosion factors provides a new tool for plant operators to identify such situations and quickly implement a process change before substantial damage has occurred and the overall process operation has been negatively impacted.

In a still further embodiment, a method is provided for determining an associated economic impact measured in terms of run time, maintenance planning and inspection requirements. For example, there has recently been an active movement to utilize KPI values ("Key Performance Indicators") as part of a real-time operational screen and information management system, which enables operators and managers of a plant to share profit-related operational information and improve the overall efficiency and profitability of the operation. When a relative degree of corrosion value is obtained as described above and evaluated together with the various KPI values, still greater safety and efficiency are achieved, thereby resulting in increased plant profitability.

It is important to appreciate that the specific means for practicing the above methods may comprise virtually any combination of known data recording and analyzing means, including but not limited to human operators, processors and microprocessors, computers, programs, analyzers, precision measuring systems and instruments, predictive control models, logic control systems, etc.

The foregoing specification is provided for illustrative purposes only, and is not intended to describe all possible aspects of the present invention. Moreover, while the invention has been shown and described in detail with respect to several exemplary embodiments, those of ordinary skill in the pertinent arts will appreciate that changes to the description, and various other modifications, omissions and additions may also be made without departing from either the spirit or scope thereof.

The invention claimed is:

1. A method of controlling corrosion-related plant operation costs, the method comprising:
   accumulating, at a controller, real-time corrosion measurements relating to a plant operation;
   calculating, at the controller, a relative degree of corrosion value based on the real-time corrosion measurements;
   comparing, at the controller, the relative degree of corrosion value to an expected corrosion progression value associated with a specified target maintenance cycle;
   adjusting, at the controller, the plant operation based on the comparison of the relative degree of corrosion value to the expected corrosion progression value; and
   determining, at the controller, an impact on a profit of the plant operation based on a cumulative effect of corrosion;
   wherein calculating the relative degree of corrosion value comprises calculating the relative degree of corrosion value as a ratio of a total accumulated corrosion present at a first time in the specified target maintenance cycle to an expected accumulated corrosion that is expected to be present at the first time, the expected accumulated corrosion based on a corrosion rate that when extended over time results in a cumulative corrosion-based end of run date that coincides with a scheduled shut-down date of the specified target maintenance cycle.

2. The method of claim 1, wherein the relative degree of corrosion value is calculated according to an equation of:

$$C(\%) = (\int_{t=0}^{t=1} d(C)/dt_{Case\,1} dt / \int_{t=0}^{t=1} EOR(d(C)/dt)_{Case\,2} dt)) * 100,$$

where C (%) is the relative degree of corrosion value, t=1 is the first time, Case 1 is the corrosion based on the real-time corrosion measurements, Case 2 is the specified target maintenance cycle, $\int_{t=0}^{t=1} d(C)/dt_{Case\,1} dt$ is the total accumulated corrosion present at the first time, and $\int_{t=0}^{t=1} EOR(d(C)/dt)_{Case\,2} dt$ is the expected accumulated corrosion that is expected to be present at the first time.

3. The method of claim 1, wherein calculating the relative degree of corrosion value further comprises calculating the relative degree of corrosion value based on a comparison of a corrosion rate present at a beginning of a plant run cycle to a corrosion rate expected to be present at a future time associated with an extended maintenance cycle.

4. The method of claim 1, further comprising calculating a total accumulated corrosion present at a second time by integrating a corrosion rate curve over a period of time ending at the second time.

5. The method of claim 1, further comprising:
   expressing the relative degree of corrosion value as a percentage value and forwarding the percentage value to an operator for use when considering shut-down of the plant operation prior to the shut-down date of the specified target maintenance cycle.

6. The method of claim 1, further comprising:
expressing the relative degree of corrosion value as a percentage value and forwarding the percentage value to an operator for use when considering a regularly scheduled shut-down of the plant operation.

7. The method of claim 1, further comprising:
expressing the relative degree of corrosion value as a percentage value and forwarding the percentage value to an operator for use when considering an assessment of quality of operations that includes consideration of corrosion-related factors.

8. The method of claim 1, further comprising:
expressing the relative degree of corrosion value as a percentage value and forwarding the percentage value to an operator for use when considering a business performance analysis that includes consideration of corrosion-related factors.

9. The method of claim 1, further comprising:
expressing the relative degree of corrosion value as a percentage value and forwarding the percentage value to an operator for use when considering a comparison of the percentage value to another percentage value obtained from a historical database.

10. The method of claim 1, further comprising:
expressing the relative degree of corrosion value as a percentage value and forwarding the percentage value to an operator for use when considering an extension of the specified target maintenance cycle.

11. The method of claim 1, further comprising:
calculating a correlative value indicative of localized corrosion; and
integrating the correlative value into the relative degree of corrosion value.

12. The method of claim 1, further comprising:
calculating a correlative value indicative of pitting; and
integrating the correlative value into the relative degree of corrosion value.

13. The method of claim 1, further comprising:
calculating a key performance indicators value; and
integrating the key performance indicators value into the relative degree of corrosion value.

14. An apparatus for controlling corrosion-related plant operation costs, the apparatus comprising:
a controller configured to:
   accumulate real-time corrosion measurements relating to a plant operation;
   calculate a relative degree of corrosion value based on the real-time corrosion measurements;
   compare the relative degree of corrosion value to an expected corrosion progression value associated with a specified target maintenance cycle;
   adjust the plant operation based on the comparison of the relative degree of corrosion value to the expected corrosion progression value; and
   determine an impact on a profit of the plant operation based on a cumulative effect of corrosion;
wherein the controller is configured to calculate the relative degree of corrosion value as a ratio of a total accumulated corrosion present at a first time in the specified target maintenance cycle to an expected accumulated corrosion that is expected to be present at the first time, the expected accumulated corrosion based on a corrosion rate that when extended over time results in a cumulative corrosion-based end of run date that coincides with a scheduled shut-down date of the specified target maintenance cycle.

15. The apparatus of claim 14, wherein the controller is configured to calculate the relative degree of corrosion value according to an equation of:

$$C(\%) = \left( \int_{t=0}^{t=1} d(C)/dt_{Case\ 1}\, dt / \int_{t=0}^{t=1} EOR(d(C)/dt)_{Case\ 2}\, dt \right) * 100,$$

where C (%) is the relative degree of corrosion value, t=1 is the first time, Case 1 is the corrosion based on the real-time corrosion measurements, Case 2 is the specified target maintenance cycle, $\int_{t=0}^{t=1} d(C)/dt_{Case\ 1}\, dt$ is the total accumulated corrosion present at the first time, and $\int_{t=0}^{t=1} EOR(d(C)/dt)_{Case\ 2}\, dt$ is the expected accumulated corrosion that is expected to be present at the first time.

16. The apparatus of claim 14, wherein the controller is configured to further calculate the relative degree of corrosion value based on a comparison of a corrosion rate present at a beginning of a plant run cycle to a corrosion rate expected to be present at a future time associated with an extended maintenance cycle.

17. The apparatus of claim 14, wherein the controller is configured to calculate a total accumulated corrosion present at a second time by integrating a corrosion rate curve over a period of time ending at the second time.

18. The apparatus of claim 14, wherein the controller is further configured to express the relative degree of corrosion value as a percentage value and to forward the percentage value to an operator.

19. The apparatus of claim 14, wherein the controller is further configured to calculate a correlative value indicative of localized corrosion and to integrate the correlative value into the relative degree of corrosion value.

20. The apparatus of claim 14, wherein the controller is further configured to calculate a correlative value indicative of pitting and to integrate the correlative value into the relative degree of corrosion value.

21. The apparatus of claim 14, wherein the controller is further configured to calculate a key performance indicators value and to integrate the key performance indicators value into the relative degree of corrosion value.

22. A non-transitory computer readable medium embodying a computer program, the computer program comprising instructions that when executed cause a processor to:
   accumulate real-time corrosion measurements relating to a plant operation;
   calculate a relative degree of corrosion value based on the real-time corrosion measurements;
   compare the relative degree of corrosion value to an expected corrosion progression value associated with a specified target maintenance cycle;
   adjust the plant operation based on the comparison of the relative degree of corrosion value to the expected corrosion progression value; and
   determine an impact on a profit of the plant operation based on a cumulative effect of corrosion;
   wherein the instructions to calculate the relative degree of corrosion value comprise instructions to calculate the relative degree of corrosion value as a ratio of a total accumulated corrosion present at a first time in the specified target maintenance cycle to an expected accumulated corrosion that is expected to be present at the first time, the expected accumulated corrosion based on a corrosion rate that when extended over time results in a cumulative corrosion-based end of run date that coincides with a scheduled shut-down date of the specified target maintenance cycle.

23. The computer readable medium of claim 22, wherein the instructions to calculate the relative degree of corrosion value comprise instructions to calculate the relative degree of corrosion value according to an equation of:

$$C(\%) = \left( {}_{t=0}\!\int^{t=1} d(C)/dt_{Case\,1}\, dt \Big/ {}_{t=0}\!\int^{t=1} EOR(d(C)/dt)_{Case\,2}\, dt \right) * 100,$$

where C (%) is the relative degree of corrosion value, t=1 is the first time, Case 1 is the corrosion based on the real-time corrosion measurements, Case 2 is the specified target maintenance cycle, ${}_{t=0}\!\int^{t=1} d(C)/dt_{Case\,1}\, dt$ is the total accumulated corrosion present at the first time, and ${}_{=0}\!\int^{t=1} EOR\,(d(C)/dt)_{case\,2}\, dt$ is the expected accumulated corrosion that is expected to be present at the first time.

\* \* \* \* \*